US 6,541,270 B2

(12) United States Patent
Singh et al.

(10) Patent No.: US 6,541,270 B2
(45) Date of Patent: Apr. 1, 2003

(54) METHOD, DETECTOR, AND APPARATUS FOR COLORIMETRIC DETECTION OF CHEMICAL AND BIOLOGICAL AGENTS

(75) Inventors: Alok Singh, Springfield, VA (US); Paul Schoen, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 52 days.

(21) Appl. No.: 09/759,149

(22) Filed: Jan. 16, 2001

(65) Prior Publication Data

US 2003/0044999 A1 Mar. 6, 2003

(51) Int. Cl.$^7$ ............................................. G01N 21/75
(52) U.S. Cl. .................... 436/166; 436/164; 436/501; 436/518; 436/523; 436/528
(58) Field of Search ................................. 436/164, 166, 436/175, 805, 501, 518, 75, 578, 523, 528; 422/55, 57, 58

(56) References Cited

U.S. PATENT DOCUMENTS

| | | | |
|---|---|---|---|
| 5,290,960 A | 3/1994 | Singh | 554/79 |
| 5,466,467 A | 11/1995 | Singh | 424/450 |
| 5,504,011 A * | 4/1996 | Gavin et al. | 422/73 |
| 5,622,872 A | 4/1997 | Ribi | 436/518 |
| 5,629,533 A * | 5/1997 | Ackley et al. | 257/103 |
| 6,001,556 A | 12/1999 | Charych et al. | 435/5 |
| 6,080,423 A | 6/2000 | Charych et al. | 424/450 |
| 6,103,217 A | 8/2000 | Charych | 424/9.321 |
| 6,387,614 B1 * | 5/2002 | Cheng et al. | 435/4 |
| 2001/0026915 A1 * | 10/2001 | Charych et al. | 435/5 |

FOREIGN PATENT DOCUMENTS

WO   WO 97/18243   * 5/1997

OTHER PUBLICATIONS

Schoen et al. "Role of giant vesicles from diacetylenic phospholipids in the development of colorimetric detection for receptor–ligand interaction", Book of Abstracts, 216th ACS Meeting Boston, Aug. 23–27 (1998), I&EC–113. American Chemical Soc.*

Ma et al. "Colorimetric Detection of *Escherichia coli* by Polydiacetylene Vesicles Functionalized with Glycolipid", J. Am. Chem. Soc., (1998), 120(48), 12678–12679.*

Magnusson et al. "Aggregation of lipid vesicles (liposomes). A versatile method to study sugar exposure on biological membranes and sugar affinity of bacteria" Acta Chem. Scand., Ser. B (1982), B36(5), 337–40 (Abstract).*

Guedj et al. "Vesicles and other supramolecular systems from biocompatible synthetic glycolipids with hydrocarbon and/or fluorocarbon chains" Chem. Phys. Lipids (1994), 72(2), 153–73.*

Kolusheva et al. "Peptide–Membrane Interactions Studied by a New Phospholipid/Polydiacetylene Colorimetric Vesicle Assay" Biochemistry (2000), 39(51), 15851–15859.*

(List continued on next page.)

Primary Examiner—Jill Warden
Assistant Examiner—Yelena Gakh
(74) Attorney, Agent, or Firm—John J. Karasek; Rebecca L. Forman

(57) ABSTRACT

A colorimetric detector for chemical and biological agents or toxins is made of a giant unilamellar vesicle (GUV) having a membrane bilayer which is polymerized to stabilize the giant unilamellar vesicle and to provide extended conjugated polymer backbone, and the GUV has at least one incorporated molecular recognition site for the chemical and biological agents or toxins. The GUVs are about 10–300 microns and preferably made of a polymerizable diacetylenic GUV where the acyl chains are crosslinked. When the agents or toxins bind to the recognition site the detector exhibits a color change. The detector can be used in a colorimetric detector apparatus where the samples can be present in air or in water.

17 Claims, 1 Drawing Sheet

OTHER PUBLICATIONS

Cheng et al. "Amino Acid Terminated Polydiacetylene Lipid Microstructures: Morphology and Chromatic Transition" Langmuir (2000), 16(12), 5333–5342.*

B. Tieke, G. Lieser, J. Colloid Interface Sci., 88, 471 (1982).

A. Singh, R. B. Thompson, J. M. Schnur, J. Am. Chem. Soc. 108, 2785 (1986).

Charych et al., Science, 261, p. 585–588 (Jul. 30 1993).

P. Yager, P. E. Schoen, Mol. Cryst. Liq. Cryst., 106, 371 (1984).

Tiecke, B., et al, J. Polym. Sci., Polym. Chem. Ed. 7, 1631–1644 (1979).

Leaver et al, Biochim. Biophys. Acta 732, 210–218 (1983).

T.G. Burke, et al., Chem. Phys. Lipids., 48, 215 (1988).

Alok Singh, Paul E. Schoen, Marie–Alice Guedeau–Boudeville, Chem. Phys. Lipids., 94, 53–61 (1998).

A. Singh and J. M. Schnur, Synth. Commun., 16, 847 (1986).

A. Singh, L. Lipid Res., 31, 1522 (1990).

M. I. Angelova, D. S. Dimitrov, Mol. Cryst. Liq. Cryst. 152, 89–104 (1987).

F.M. Menger and S.J. Lee, Langmuir, 11, 3685–3689 (1995).

* cited by examiner

METHOD, DETECTOR, AND APPARATUS FOR COLORIMETRIC DETECTION OF CHEMICAL AND BIOLOGICAL AGENTS

FIELD OF THE INVENTION

This invention relates to the use of giant unilamellar vesicles (GUV) in the colorimetric detection of chemical and biological agents by simple receptor-ligand interaction.

BACKGROUND OF THE INVENTION & DESCRIPTION OF RELATED ART

Diacetylenes and their analogues upon polymerization produce a deep blue colored polydiacetylene polymer. The presence of conjugated single, double, and triple bonds in polydiacetylene backbone is responsible for the deep color. See B. Tieke, G. Lieser, J. Colloid Interface Sci., 88, 471(1982).

A blue to red color shift in polymer-backbone is observed when the polymer goes through mechanical or thermal stress. See A. Singh, R. B. Thompson, J. M. Schnur, J. Am. Chem. Soc. 108, 2785(1986). This stress associated color change in polydiacetylenic backbone has been used in the development of various detector and sensor schemes.

This idea has been extended to the detection of molecular species which cause stress on the polymer backbone upon binding to the molecular sites covalently attached to the polydiacetylene backbone. For example, polydiacetylene films containing glycolipid sites have been used in the detection of biological species such as cholera toxin. See Charych et al., Science, 261, p. 585–588 (Jul. 30, 1993).

The conventional approach of thin polydiacetylenic film faces the difficulty of making the thin film and then transferring it onto a substrate. Reading the film spectrophotometrically poses an additional problem. The film is generally deposited on the glass slide substrate and the binding experiment is done in the solution for about 20 minutes. The color changes are read spectrophotometrically, a cumbersome process which may lead to some inaccuracies due to changes in the medium during the course of the experiment.

Vesicles serve as the best substrates because of their large surface area, good dispersion behavior, and availability of surface available receptor sites for toxins. But the diacetylene moiety in a small vesicle does not polymerize efficiently due to its small radius of curvature. Therefore color changes due to stress on the polymer backbone, transferred by ligand binding, may not be visible.

Multilamellar vesicles (MLVs) may polymerize better than small unilamellar vesicles (SUVs), but they will partially transform into other structures such as tubules in most cases when cooled below their phase transition temperature. See P. Yager, P. E. Schoen, Mol. Cryst. Liq. Cryst., 106, 371(1984). This cooling step is needed to permit topotactic polymerization of diacetylene. Topotactic polymerization relates to ordering the neighboring polymerizable diacetylenic functionalities in a parallel to each other fashion. This ordering is acquired in diacetylene containing chains by cooling the lipid vesicles below their phase transition temperature or $T_m$. See Ticke, B., et al, J. Polym. Sci., Polym. Chem. Ed. 7, 1631–1644 (1979) and Lever et al, Biochim. Biophys. Acta 732, 210–218 (1983).

The diacetylenic SUVs do remain stable at temperatures down to about 2.4° C., almost 40 degrees below $T_m$, where differential scanning calorimetry shows that a phase transformation occurs. See T. G. Burke, et al., Chem. Phys. Lipids., 48, 215 (1988). Although these small vesicles do not turn into tubules upon cooling, as discussed above, these SUV diacetylenes fail to polymerize to provide an extended conjugation due to curvature constraints. Such extended conjugation is desired to provide darker color which results in better visibility.

Giant unilamellar vesicles (GUVs) produced from diacetylenic phospholipid, 1,2 bis (heptacosa-8,10-diynoyl)-sn-glycero-3-phosphocholine ($DC_{6,15}PC$) have recently been prepared which are generally 10 to 100 times larger than typical vesicles by applying an electric field to the aqueous dispersion maintained above its chain melting transition temperature ($T_m$) of 58.9° C. See Alok Singh, Paul E. Schoen, Marie-Alice Guedeau-Boudeville, Chem. Phys. Lipids., 94, 53–61 (1998). There has been no disclosure of these new GUVs being used in colorimetric sensors.

OBJECTS OF THE INVENTION

It is an object of this invention to produce giant unilamellar vesicles (GUVs) with a large radius of curvature which can polymerize effectively.

It is a further object of this invention to produce giant unilamellar vesicles with a large radius of curvature which are polymerized and which have a polymer membrane that allows the free transport of contents across the membrane bilayer so as to eliminate the risk of any color change due to osmotic shock.

It is a further object of this invention to produce giant unilamellar vesicles with a large radius of curvature which are polymerized and large in size so they may be handled and manipulated individually.

It is a further object of this invention to produce giant unilamellar vesicles with a large radius of curvature which have a size of at least 50 microns.

It is a further object of this invention to produce a colorimetric detector of chemical and biological agents utilizing giant unilamellar vesicles with a large radius of curvature so as to make customized arrays to enhance detection.

It is a further object of this invention to produce a colorimetric detector of chemical and biological agents utilizing giant unilamellar vesicles with a large radius of curvature so that individual giant unilamellar vesicles may be probed for color change due to site specific binding.

These and further objects of the invention will become apparent as the description of the invention proceeds.

SUMMARY OF THE INVENTION

A colorimetric detector for chemical and biological agents or toxins is made of a giant unilamellar vesicle (GUV) having a membrane bilayer which is polymerized to stabilize the giant unilamellar vesicle and to provide extended conjugated polymer backbone, and there is at least one incorporated molecular recognition site for the chemical and biological agents or toxins. The GUV is preferably a polymerizable diacetylenic GUV. In this case, the polymerization to stabilize the giant unilamellar vesicle is done by crosslinking the acyl chains in the membrane bilayer of the diacetylenic GUV. Upon the binding by the chemical and biological agents or toxins, the detector exhibits a color change in the visible region of the spectrum. Examples of incorporated molecular recognition sites are di or polysaccharides substituted with a long alkyl chain preferably containing diacetylenic moiety. Preferable examples are N-octadecyl maltobionamide (C-18 maltonamide) and N-octadecyl lactobionamide (C-18 lactonamide). The GUV is preferably made from 1,2 bis-(alkadiynoyl)-sn-glycero-3-phosphocholine ($DC_{m,n}PC$) where m=2–16 and n=7–16, and m+n≧20 carbon atoms. A particularly preferred material is 1,2 bis-(Tricosa-10,12-diynoyl)-sn-glycero-3-phosphocholine ($DC_{8,9}PC$). The GUV in the detector has a large radius of curvature of at least 50 microns and the size of the GUV is about 10–300 microns. The large radius of curvature refers to the surface of the vesicles being flat. Small vesicles have a curved surface because they have a small radius of curvature. Vesicles having a diameter of at least 1 micron are considered to have a large radius of curvature. The GUV can be used on a substrate to detect the presence of specific species or it can be used by itself as a substrate to detect the presence of specific species.

The colorimetric detector is used for the detection of chemical and biological agents or toxins in a test sample by exposing the test sample to the colorimetric detector which is made of giant unilamellar vesicles (GUV) having a membrane bilayer which is polymerized to stabilize the giant unilamellar vesicle and to provide extended conjugated polymer backbone and which has at least one incorporated molecular recognition receptor site for the chemical and biological agents or toxins. As a result of the interaction of the chemical and biological agents with the receptor sites a colorimetric detection signal is produced.

The colorimetric detector can be used in a colorimetric detector apparatus for detecting chemical and biological agents or toxins. The apparatus has a chamber with a series of passageways for analyzing the sampling fluid containing the colorimetric detector described above. There is a chamber inlet for sampling a fluid containing the chemical and biological agents or toxins, a means for reading the output of the colorimetric detector, and a chamber outlet for the sampling fluid. The different passageways can have different detectors for various agents and toxins. The passageways can have an inlet filter which can preferably be a 2–10 micron filter and a similar filter can be used on the outlet side of the passageway. The passageway can have capillaries filled with the GUVs. The colorimetric detector apparatus can have a window for optical read out and a commercial monitor can be used to read the output of the colorimetric detector. The detector is capable of handling samples present in air or in water.

DESCRIPTION OF THE PREFERRED EMBODIMENTS

Figure 1:
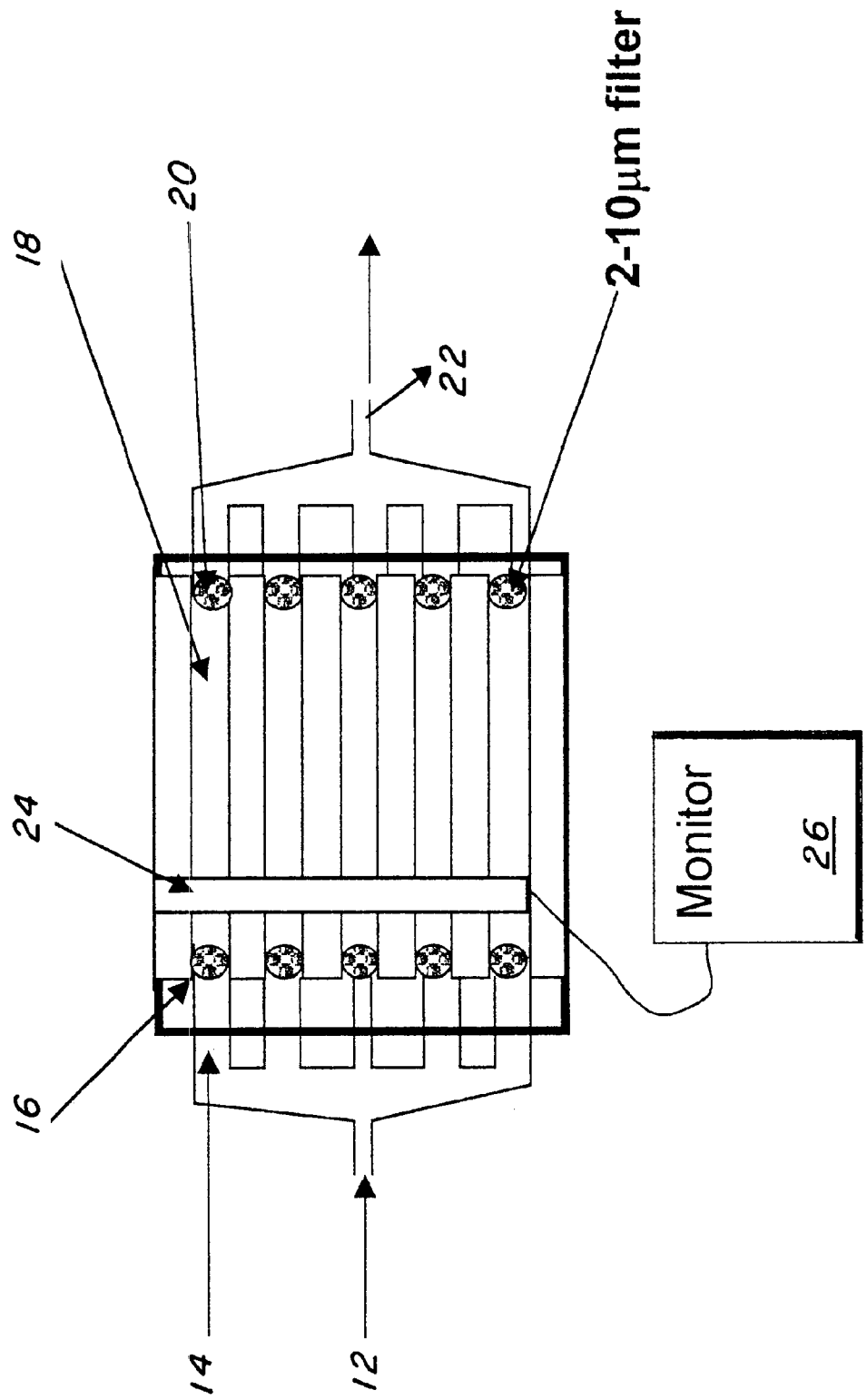
FIG. 1 illustrates a device for monitoring samples by using the colorimetric detector.

The GUV has been receiving much attention recently in the literature. They are vesicles with diameters of about 10–300 microns. One reason fot the attention is because it transforms what has always been a microscopic object, the vesicle, into something on a macroscopic scale of up to 2–3 tenths of a millimeter in diameter. With this relatively large radius of curvature the GUV still maintains a single bilayer wall thickness. The GUV has become a robust, transportable version of the Langmuir Blodgett (LB) film at the air-water interface.

We have found diacetylenic lipids provide a stable vesicular form over a wide temperature range below their phase transition temperature, so it allows experimentation with non-tubular morphology below $T_c$. As to nomenclature, when cooling the hot lipid dispersion to room temperature acyl chains of the lipid transform from melted to crystalline phase. Temperature at which this transition is observed is called $T_c$. It is similar to the transition temperature when the crystalline chains melts upon heating the dispersion also called melting transition temperature $T_m$. Previously, all but the smallest vesicles of this lipid would transform into tubules below the phase transition temperature. We have found that by polymerizing these GUVs they do not collapse at room temperature and that the polymerization provides both stability and improved color.

While investigating GUVs, we have found that GUVs are polymerizable and that GUVs are porous. We have also found that GUVs can be functionalized. The preferred diacetylenic GUVs in their polymerized form are a permanent plastic bubble which resembles a real life soap bubble, they are freeze-dryable, they are a stable platform, and they are highly porous. The advantage of having a porous vesicle means that a change in the surrounding medium will not give an osmotic shock to the vesicle and therefore disrupt the sensing mechanism. The GUVs provide a hospitable environment for biomolecules, maintaining hydration which preserves functions for enzymes, for instance.

We have further found these GUVs by virtue of their size and lack of stringent curvature, and due to their relatively large radius of curvature lead to extensive polymerization and thus produce longer conjugation polymers which are superior for detection. Such a longer unstressed conjugated polymeric backbone produces better signal and bigger changes upon binding of linked ligand sites to pathogens as opposed to small vesicles or polymeric films.

The production of a colorimetric detector based on the GUV is done in a series of steps. First, a lipid which will form a giant unilamellar vesicle (GUV) is dissolved in a solvent along with a glycosurfactant that will serve as a molecular recognition site. Next the solvent is removed to produce a film with the glycosurfactant incorporated in the lipid. Then the film is hydrated and subjected to conditions to form a GUV. A preferred condition is treating the mixture to an alternating electric field while maintaining the temperature above the chain melting transition temperature of the lipid to produce electrical swelling and formation of the GUV. Then the GUV is polymerized to obtain a stabilized colorimetric detector. The resulting colorimetric detector can be tested by demonstrating the specific binding affinity of toxins to surface bound glycolipids on the polymerized giant vesicles.

To prepare the Giant Unilamellar Vesicles a lipid having the formula $DC_{m,n}PC$:

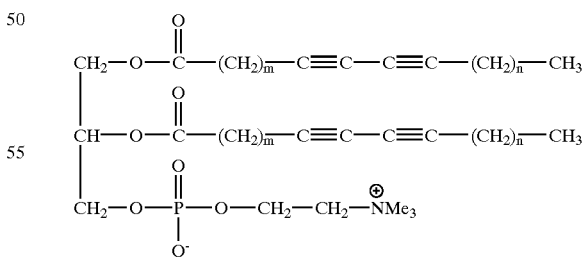

(where m and n represent the number of methylene groups before and after diacetylenic moiety in the acyl chain and where m=2–16, n=7–22, and m+n=16–29) was used and it was prepared by following a published procedure. See A. Singh and J. M. Schnur, Synth. Commun., 16, 847 (1986) and A. Singh, L. Lipid Res., 31, 1522 (1990). In this publication the lipid used was a diacetylenic phospholipid 1,2 bis (heptacosa-8,10-diynoyl)-sn-glycero-3-phosphocholine ($DC_{6,15}PC$) having the chemical structure:

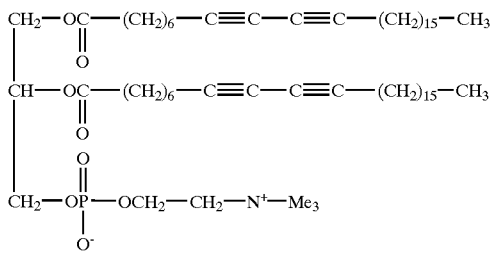

In the nomenclature for this compound D means "di" or two and C refers to "carbon chain" thus DC is a twin carbon chain. The notation m,n refers to th number of methylenes above (proximal to the head group) and below the diacetylene group in the acyl moiety as shown in the formula above.

In the following examples unilamellar, spherical giant vesicles from $DC_{6,15}PC$, and saturated distearoyl phosphatidylcholine (DSPC) were prepared by following a reported procedure modified to this application. See M. I. Angelova, D. S. Dimitrov, Mol. Cryst. Liq. Cryst. 152, 89–104 (1987).

The preferred diacetylenic GUVs are prepared by treating the lipid to an alternating electric field while being heated to produce electrical swelling and formation of the GUVs. The GUVs were cooled below their $T_c$ temperature and polymerized for stability.

Having described the basic aspects of the invention, the following examples are given to illustrate specific embodiments thereof.

EXAMPLE 1

This example illustrates a preferred method for producing a GUV. A 10 ml chloroform/methanol (9:1) solution (10 mg/ml) of a lipid having the formula $DC_{m,n}PC$:

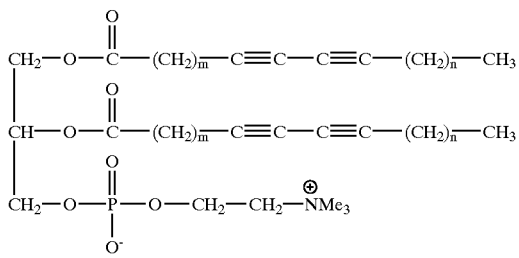

where m and n represent the number of methylene groups before and after diacetylenic moiety in the acyl chain was spread on two conductive In—$SnO_2$-coated glass plates (3.5 cm×1 cm) and then dried under high vacuum for approximately 1 hour to obtain a thin lipid film. The plates were then fixed, face-to-face, about 1 mm apart, by sandwiching a Viton rubber spacer between them. After applying an 0.5 V, 10 Hz AC voltage (Hewlett Packard 332A Function Generator) the cell was filled with a 50 mM sucrose solution and the aperture was sealed with Vitrex.

This sealed cell was placed in an oven at 72° C., during the process of electrical swelling. The alternating-current voltage was increased slowly from 0.5 V to 1.5 V over 1 hour. After 6 hours the frequency was decreased to 5 Hz and the swelling was continued for an additional 4 hours.

The GUVs thus produced were stored at 72° C. The giant vesicles were observed by a reverse-phase microscope (Nikon Diaphot-TMD, objective×20). When the lipid was a diacetylenic phospholipid 1,2 bis (heptacosa-8,10-diynoyl)-sn-glycero-3-phosphocholine ($DC_{6,15}PC$) the average diameter vesicles obtained were >100 µm.

Diacetylenes in bilayers polymerize efficiently below their chain melting transition temperature $T_m$ because at this lower temperature all of the chains are extended to attain an all-trans conformation, which is needed for polymerization to occur. Smaller multilamellar vesicles (MLVs) usually transform into tubule structures when cooled just below their phase transition temperature $T_m$.

EXAMPLE 2

This example illustrates the stability of the GUV on cooling and demonstrates GUVs can be cooled down to about 28° C. below their $T_m$ without losing their morphology. This permits production of longer conjugation and consequently good color.

GUVs as made in Example 1 from $DC_{6,15}$ PC upon slow-cooling below their $T_m$ did not show any morphology transformation. They remained as bubbles and did not become tubules, smaller vesicles or simply flat sheets. The effect of cooling on the morphology was studied by using optical microscopy. The swelling cell, which is the container in which GUVs are created, produces many giant vesicles with diameters up to about 300 micrometers, was directly placed in a temperature regulated support connected to a thermostated bath. The temperature changes were monitored by a microcomputer thermometer. The thermocouple was inserted between the cell and the regulated heating support, which provided accurate readings of the cell temperature. GUVs were examined for morphological changes by lowering the temperature from 70 to 30° C. as it was cooled from 70 to 30° C. at a rate of about 1° C./min.

A series of video images were taken and examined by optical microscopy of a 260 micrometer diameter GUV of the diacetylenic lipid which showed at what temperature the GUV began to rupture and collapse. For, example, six photos taken at the following temperatures: 32.1° C.; 31.9° C.; 31.8° C.; 31.6° C.; 31.55° C.; 31.5° C. At 32.1° C. a dark spot appeared at the equator of the spherical vesicle. This could be the weak part of the membrane caused by the defect due to mismatch in lipid registering with the next molecule. Disintegration of the an membrane began at this point, spreading rapidly all around the circumference of the vesicle, resulting in a lipid aggregate of unknown morphology. These photos show that the collapse occurs at a triggering temperature and the collapse occurs rapidly. These images illustrate the progress of collapse. There is only a minute amount of time for the temperature to change during the collapse.

MLVs of $DC_{6,15}PC$ with diameters near 1 micrometer and Large Unilamellar Vesicles (LUVs) which are vesicles with diameters equal to or more than 1 micrometer transform into tubules near $T_m$ at 59° C. GUVs, on the other hand, with much larger diameters of 200 micrometers or more disintegrate at a temperature 26 degrees cooler than its $T_m$. Thus the large radius of curvature of the GUV accompanies a larger temperature window of stability below $T_m$ for the vesicular structures and facilitates efficient polymerization at the same time.

This example illustrates the unique shape of the GUV. Unlike the SUV or the MLV, the GUV retains its shape upon cooling to far below its $T_m$ until it finally collapsed.

EXAMPLE 3

This is a comparative example illustrating the effect of cooling on saturated 1,2 distearoyl phosphatidylcholine (DSPC).

Saturated 1,2 distearoyl phophatidylcholine (DSPC) having the formula:

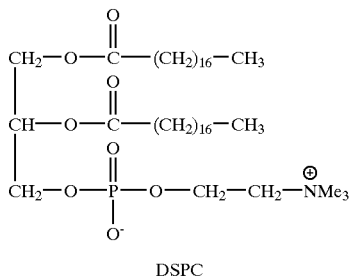

DSPC was cooled from 60.0° C. to 42.0° C. and rate of cooling was 1° C./min. The liquid to gel phase transition temperature $T_m$ occurred at 47.8° C.

This example illustrates the difference between diacetylenic GUVs as evaluated in Example 2 and DSPC GUVs and it illustrates the uniqueness of a GUV derived from a diacetylenic lipid. Saturated DSPC GUVs don't shrunk in size upon cooling so they are stable, but they have no color. The reason for this is that upon polymerization diacetylene produces deep blue to red color showing that diacetylenes are polymerized to conjugated polydiacetylene. The DSPC, on the other hand, does not polymerize because it doesn't have any diacetylene functionality. The diacetylenic GUVs do not gel like saturated DSPC GUVs and they are not stable down to room temperature such that they will collapse unless they are polymerized. However, as will be illustrated in the next example, polymerization solves that stability problem.

Polymerization of GUVs of $DC_{6,15}$ PC can be performed by directly irradiating the sample cell with UV light from a mercury pen lamp.

EXAMPLE 4

This example illustrates that GUVs do not change morphology upon cooling $<T_m$, a temperature necessary for polymerizing vesicles and it serves to demonstrate efficient polymerization.

Polymerization of GUVs of $DC_{6,15}$ PC was performed by directly irradiating a sample cell with UV light from a mercury pen lamp. The temperature was maintained at 50° C., well below $T_m$ (59° C.), so the lipid would be in its low temperature ordered phase. In this phase the acyl chains will be in the all-trans configuration, with their diacetylenic units packed close together, which is the favorable alignment required for topotactic polymerization. As the polymerization progressed, the contrast of the GUV in the optical images began to decrease. After about 30 seconds had passed, the contrast had dropped substantially, and the GUV had become very difficult to distinguish from the surrounding medium. The initial high contrast was because inside the vesicle the contents are different from outside. The subsequent lower contrast means the GUV has become porous and the inside and outside content are the same.

This example confirms that GUVs polymerize efficiently leaving a highly permeable membrane which is stable at lower temperature. This high permeability is suitable for a detection system because unrestricted transport of medium across bilayers will not cause any a osmotic shock, which could have caused some stress on the polydiacetylene backbone.

The following examples illustrate the molecular recognition involving an interaction between polymerizable vesicles made from 1,2 bis-(Tricosa-10,12-diynoyl)-sn-glycero-3-phosphocholine and two molecular recognition (receptor) sites N-octadecyl lactobionamide (C-18 lactonamide) and N-octadecyl maltobionamide (C-18 maltonamide) with two chemical and biological ligands in the form of lectins, concovalin A (ConA) and peanut agglutinin (PNA).

EXAMPLE 5

This example describes how vesicles with surface bound glycolipids were prepared.

Two glycosurfactants, derived from disachharide maltose and lactose, N-octadecyl maltobionamide (C-18 maltonamide) and N-octadecyl lactobionamide (C-18 lactonamide) were incorporated in the polymerizable diacetylenic phospholipid ($DC_{8,9}PC$) vesicles. The vesicles contained 5 mol percent glycosurfactant incorporated in them. Typically, 5.7 mg glycosurfactant and 17.4 mg polymerizable lipid, DC8,9PC, were dissolved in 10 mL (1:1) chloroform:methanol. The solvent was then removed in a slow stream of nitrogen gas leaving behind a thin film. The thin film of lipid was hydrated by adding 10 mL of appropriate buffer solution (Tris HCl, pH 6.4 for C-18 maltobionamide and Phosphate buffer, pH 7.4 for C-18 lactobionamide). Hydration was completed by heating at 30° C. for 30 minutes followed by brief sonication to ensure uniform dispersion. Typical concentration of the lipid in dispersion was kept around 2 mg/mL. After this insertion of the glycolipid into vesicle membrane the vesicles were then polymerized by exposing to 254 nm light. Any large pieces in the dispersion were removed by centrifuging the vesicle dispersion.

EXAMPLE 6

This example describes specific binding affinity of toxins to surface bound glycolipids.

The specificity of surface available galactose or glucose functionality of the two surfactants used to make the two vesicles with surface bound glycolipids in Example 6 was examined by exposing them to two lectins PNA (galactose specific) and ConA (glucose specific).

For sugar-lectin binding assays, a dilute solution of lectin (concentration was chosen arbitrarily) was prepared in appropriate buffer. The tris buffer was used for Con A and the phosphate buffer was used for PNA lectin. Agglutination or binding affinities were measured by adding 100 ml lectin solution to 400 ml vesicle dispersion and then recording the absorption at 400 nm against time until a plateau is obtained.

The results showed for the binding of lectins with sugar head-groups incorporated in the polymerized vesicles there was a binding affinity between C-18 maltonamide and Con A and a binding affinity between C-18 lactonamide and PNA.

The polymerized vesicles by themselves do not show any affinity towards either ConA or PNA (data not shown). The results also showed a negative affinity between lactonamide and ConA and a negative affinity between maltonamide and PNA.

The detection scheme described above has been with the sample in an aqueous medium. Using just dry vesicles will not show a color change upon binding. However, the vesicles can be stored in freeze-dried form for a long period and then they can be hydrated before use.

A device which can monitor either samples in the air or in a liquid is illustrated in FIG. 1.

The detector in FIG. 1 has an inlet (12) through which either air or water can be introduced. The fluid flows into a series of passageways (14) which have an inlet filter 16 which can be a 2–10 micron filter and then into capillaries (18) filed with GUVs containing receptors specific for individual toxins. The GUVS are preferably in buffer or water. The fluid leaves the passageways through an outlet filter (20) which can be the same type as the inlet filter (16) and finally the fluid exits through the device outlet (22). The device can have a quartz or glass window (24) for optical read out and a monitor (26) can be used. Color changes can also be monitored by using a portable commercial spectrophotometer.

The current approach involving giant unilamellar vesicles is far superior for color detection for the following reasons. The giant unilamellar vesicles with their large radius of curvature will polymerize well. The polymer membrane of the GUV allows free transport of contents across membrane bilayer, which eliminates the risk of any color change due to osmotic shock. The GUVs may be handled and manipulated individually due to their relatively large size. This ability to add various receptors to the GUVs permits making customized arrays to enhance detection. Finally, each individual GUV may be probed for color change due to its site specific binding.

It is understood that the foregoing detailed description is given merely by way of illustration and that many variations may be made therein without departing from the spirit of this invention.

What is claimed is:

1. A colorimetric detector for chemical and biological agents or toxins, comprising:

a giant unilamellar vesicle (GUV) derived from 1,2 bis-(alkadiynoyl)-sn-glycero-3-phosphocholine ($DC_{m,n}PC$) where m=2–16 and n=7–16, and m+n≧20 carbon atoms;

wherein the GUV has a large radius of curvature of at least 50 microns;

wherein the size of the GUV is from 10 to 300 microns; and wherein the GUV has a membrane bilayer that is polymerized by crosslinking acyl chains in the membrane bilayer to stabilize the GUV and to provide extended conjugated polymer backbone; and at least one incorporated molecular recognition site for said chemical and biological agents or toxins consisting of N-octadecyl maltobionamide (C-18 maltonamide) or N-octadecyl lactobionamide (C-18 lactonamide) wherein a colorimetric detection signal is produced when the chemical or biological agent or toxin binds with the molecular recognition site.

2. A colorimetric detector according to claim 1, wherein the GUV is a polymerizable diacetylenic GUV.

3. A colorimetric detector according to claim 1, wherein the GUV is made from 1,2 bis-(tricosa-10,12-diynoyl)-sn-glycero-3-phosphocholine $DC_{8,9}PC$.

4. A colorimetric detector according to claim 1, wherein the GUV is used on a substrate to detect the presence of specific chemical species.

5. A colorimetric detector according to claim 1, wherein the GUV is used by itself as a substrate to detect the presence of specific chemical species.

6. A method for colorimetric detection of chemical and biological agents or toxins in a test sample, comprising:

exposing said test sample to giant unilamellar vesicles (GUV) derived from 1,2 bis-(alkadiynoyl)-sn-glycero-3-phosphocholine ($DC_{m,n}PC$) where m=2–16 and n=7–16, and m+n≧20 carbon atoms;

wherein the GUV has a large radius of curvature of at least 50 microns;

wherein the size of the GUV is from 10 to 300 microns; and wherein the GUV has a membrane bilayer that is polymerized by crosslinking acyl chains in the membrane bilayer to stabilize the GUV and to provide extended conjugated polymer backbone; and at least one incorporated molecular recognition receptor site for said chemical and biological agents or toxins consisting of N-octadecyl maltobionamide (C-18 maltonamide) or N-octadecyl lactobionamide (C-18 lactonamide), whereby the binding of the chemical and biological agents with the receptor sites produces a colorimetric detection signal; and detecting said signal.

7. A method of detecting chemical and biological agents according to claim 6, wherein the GUV is a polymerizable diacetylenic GUV.

8. A colorimetric detector apparatus for detecting chemical and biological agents or toxins comprising:

a chamber having a series of passageways for analyzing the sampling fluid containing the colorimetric detector of claim 1, a chamber inlet for sampling a fluid containing chemical and biological agents or toxins, means for reading the output of the calorimetric detector, and a chamber outlet for the sampling fluid.

9. A colorimetric detector apparatus according to claim 8, wherein different passageways have different detectors for various agents or toxins.

10. A colorimetric detector apparatus according to claim 8, wherein each passageway has an inlet filter.

11. A calorimetric detector apparatus according to claim 10, wherein the inlet filter has a 2–10 micron filter.

12. A colorimetric detector apparatus according to claim 8, wherein each passageway has capillaries filled with the GUVs.

13. A colorimetric detector apparatus according to claim 8, wherein each passageway has an outlet filter.

14. A calorimetric detector apparatus according to claim 13, wherein the outlet filter has a 2–10 micron filter.

15. A calorimetric detector apparatus according to claim 8, wherein the means for reading the output of the colorimetric detector is a window for optical read out.

16. A calorimetric detector apparatus according to claim 8, wherein the means for reading the output of the colorimetric detector further comprises a commercial monitor.

17. A colorimetric detector apparatus according to claim 8, wherein the fluid inlet and outlet are capable of handling samples present in air or in water.

* * * * *